United States Patent
Yu et al.

(10) Patent No.: US 9,511,013 B2
(45) Date of Patent: Dec. 6, 2016

(54) HERBAL COMPOSITION FOR SKIN-WHITENING AND ANTI-SKIN-AGING, METHOD OF PREPARATION AND THE USE THEREOF

(71) Applicant: Hong Kong Baptist University, Hong Kong (HK)

(72) Inventors: Zhiling Yu, Hong Kong (HK); Hua Yu, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 13 days.

(21) Appl. No.: 14/191,470

(22) Filed: Feb. 27, 2014

(65) Prior Publication Data

US 2014/0242013 A1 Aug. 28, 2014

(30) Foreign Application Priority Data

Feb. 28, 2013 (CN) .......................... 2013 1 0063194

(51) Int. Cl.
*A61K 8/97* (2006.01)
*A61Q 19/08* (2006.01)
*A61Q 19/02* (2006.01)

(52) U.S. Cl.
CPC ............... *A61K 8/97* (2013.01); *A61Q 19/02* (2013.01); *A61Q 19/08* (2013.01); *A61K 2800/5922* (2013.01)

(58) Field of Classification Search
None
See application file for complete search history.

(56) References Cited

U.S. PATENT DOCUMENTS

2008/0152734 A1* 6/2008 Miyake et al. ............... 424/757
2008/0241200 A1* 10/2008 Sojka ........................... 424/401

FOREIGN PATENT DOCUMENTS

| CN | 102198078 | * | 9/2011 |
| CN | 102805721 | * | 12/2012 |
| KR | 102012009529 9 | * | 10/2012 |

OTHER PUBLICATIONS

English Machine Translation of CN 102805721, pp. 1-5, retrieved from espacenet.com on Jun. 29, 2015.*
English Machine Translation of KR 1020120095299, pp. 1-23, retrieved from espacenet.com on Jun. 29, 2015.*
Liu et al. Machine translation for CN102198078 [online]. Google Patents, 2016 [retrieved on Jan. 12, 2016]. Retrieved from the Internet: <https://www.google.com/?tbm=pts&hl=en&gws_rd=ssl>.*

* cited by examiner

Primary Examiner — Richard Schnizer
Assistant Examiner — Katherine Peebles
(74) Attorney, Agent, or Firm — Ella Cheong Hong Kong; Sam T. Yip

(57) ABSTRACT

This invention provides a Chinese medicinal formula comprising *Atractylodis Macrocephalae Rhizoma, Glycyrrhizae Radix et Rhizoma, Angelicae sinensis Radix, Paeoniae Radix Alba* and *Poria* for skin care. It further relates to a method for preparing bioactive fraction of this formula and to the applications of the bioactive fraction in skin-whitening and anti-skin-aging.

4 Claims, 4 Drawing Sheets

HERBAL COMPOSITION FOR SKIN-WHITENING AND ANTI-SKIN-AGING, METHOD OF PREPARATION AND THE USE THEREOF

CROSS-REFERENCE TO RELATED APPLICATIONS

The present application claims the benefit of China patent application number 201310063194.5 filed Feb. 28, 2013, disclosure of which is incorporated herein by reference in its entirety.

FIELD OF THE INVENTION

The present invention relates to a skin care composition. Particularly, the present invention relates to the use of said skin care composition for skin whitening and anti-skin aging. The present invention also discloses method of preparation of said composition from bioactive fraction of Chinese medicinal herbs.

BACKGROUND OF THE INVENTION

White and light skin is preferred by the majority of people. Numerous skin-care products for skin-whitening and anti-skin-aging have been developed for both cosmetic and medicinal applications. However, products containing synthesized chemicals always carry adverse effects. For example, hydroquinone-containing products for skin bleaching exhibit adverse effects such as exogenous ochronosis and leukoderma-en-confetti/occupational vitiligo. Since 2001, hydroquinone has been forbidden in the European Union to be used as an ingredient for cosmetics. In addition, some natural components-containing products also exhibit some disadvantages for skin care. For examples, kojic acid is not stable and causes skin irritations; and arbutin presents weak effect in skin-whitening.

Oxidative stress plays a central role in initiating and driving events that cause skin aging at cellular level. It has been widely accepted that the formation of free radicals plays a pivotal mechanism leading to skin aging. Scavenging of reactive oxygen species can protect skin cells from free radicals induced damages. Currently, topical antioxidants, such as vitamin A, have been widely used in over-the-counter skin care products. However, vitamin A-containing products have adverse effects including redness, scaling, burning, and itching.

Therefore, development of a tailored product with high potency for skin-whitening and anti-skin-aging has been focused by many researchers and cosmetic industries.

Skin color is determined by the content of melanin dispersed in epidermis. Biosynthesis of melanin (also called melanogenesis) occurs in melanocytes and catalyzes by three enzymes named tyrosinase (TYR), tyrosinase related protein-1 (TRP-1) and tyrosinase related protein-2 (TRP-2). Among them, TYR has been identified as the rate-limiting enzyme for melanin biosynthesis. Inhibition of cellular TYR activity can effectively decrease melanogenesis thus whitening the skin. Most current commercial cosmetic products for skin-whitening are TYR inhibitors.

Biologically, the transcription of genes encoding TYR and TRP-1 is under the control of microphthalmia transcription factor (MITF), which is regulated by the Wnt signaling pathway, the p38 signaling pathway and the mitogen-activated protein (MAP) kinase pathways as well as by cyclic adenosine 3',5'-monophosphate/protein kinase A/cAMP response element binding protein (cAMP/PKA/CREB) pathway. Any agents that regulate these signaling pathways also have the potential to affect MITF thus melanogenesis. Therefore, combination of different compounds with multi-targets for regulating MITF is more effective on skin-whitening than single compound with single target.

Improvement of the skin conditions, i.e. anti-skin-aging, to accelerate melanin elimination from the epidermis is another strategy for skin-whitening. Scavenging of free radicals can help skin-whitening and prevent skin aging. A good skin-care product should have multiple functions such as skin-whitening and anti-skin-aging.

Citation or identification of any reference in this section or any other section of this application shall not be construed as an admission that such reference is available as prior art for the present application.

SUMMARY OF INVENTION

According to a first aspect of the present invention, there is provided a composition for skin-care, comprising Chinese herb from *Atractylodis Macrocephalae Rhizoma, Glycyrrhizae Radix et Rhizoma, Angelicae sinensis Radix, Paeoniae Radix Alba* and *Poria*.

In accordance with one aspect of the present invention, there is provided a method for extraction and separation of fractions and compounds from a natural source;

In another aspect of the present invention, there is provided a treatment for skin related to skin whitening and/or anti-skin-aging, which comprising using a therapeutic effective amount of bioactive fractions of Chinese herbs, or a mixture thereof.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

Figure 1:
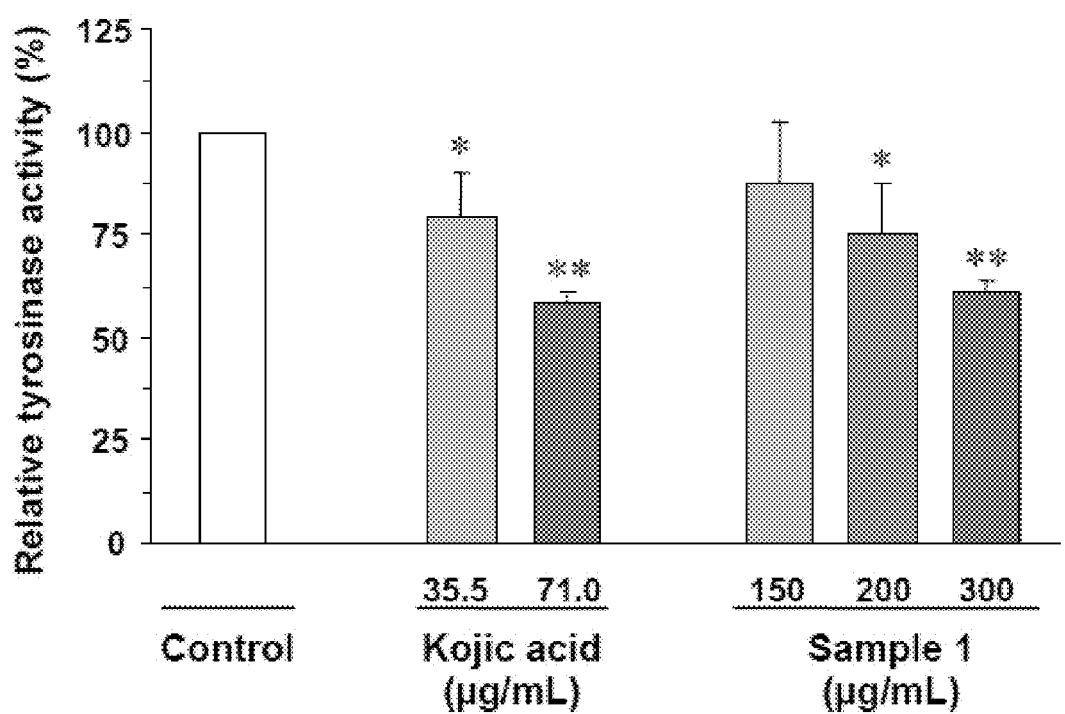
FIG. 1 shows the dose-dependently inhibitory effect of an embodiment of the herbal extract (sample 1 in Table 2a) on cellular tyrosinase activity inhibition in B16 cells. Kojic acid is used as positive control. Data are expressed as Mean±SD (n=3). *$p<0.05$ vs control; **$p<0.01$ vs control.

Chinese medicine has been identified as one of the entries for skin care purpose. The present invention provides the use of bioactive fractions of combined Chinese herbs to resolve the problems of skin pigmentation and aging.

Five medicinal herbs including *Atractylodis Macrocephalae Rhizoma, Glycyrrhizae Radix et Rhizoma, Angelicae sinensis Radix, Paeoniae Radix Alba* and *Poria* have various functions, for example, *Glycyrrhizae Radix et Rhizoma* has anti-inflammatory and anti-oxidative properties. They have been used for thousands of years and have been identified to be safe and effective for treating various diseases. However, uses of the combination of these herbs for skin-whitening and anti-skin-aging have not yet been disclosed.

The present invention provides a composition comprising *Atractylodis Macrocephalae Rhizoma, Glycyrrhizae Radix et Rhizoma, Angelicae sinensis Radix, Paeoniae Radix Alba* and *Poria* for skin-whitening and/or anti-skin-aging and method for skin whitening and anti-skin aging comprising applying said composition to a subject in need thereof. The present composition is applied to the subject in need thereof via topical administration. The present composition is in the form of a day cream, a night cream, a face lotion, a body lotion, a body butter, a skin peel, a mask, a shower gel, a sun cream, a sun lotion, an after sun cream or an after sun lotion.

In one embodiment, the present composition comprises *Atractylodis Macrocephalae Rhizoma* at an amount ranging from about 5 to about 30, from about 15 to about 25, or at about 20, % by weight. In another embodiment, *Glycyrrhizae Radix et Rhizoma* is present at an amount ranging from about 1 to about 20, from about 5 to about 15, or at about 10, % by weight. In yet another embodiment, *Angelicae sinensis Radix* is at present an amount ranging from about 5 to about 75, from about 15 to about 75, from about 15 to about 60, or at about 30, % by weight. In another embodiment, *Paeoniae Radix Alba* is present at an amount ranging from about 5 to about 30, from about 15 to about 25, or at about 20, % by weight. In another embodiment, *Poria* blend is present at an amount ranging from about 5 to about 30, from about 15 to about 25, or at about 20, % by weight.

Determinations of Cellular Tyrosinase Activity and Melanin Production in Murine B16 Cells Murine B16 cells (Shanghai Institutes for Biological Science, Chinese Academy of Sciences, China) are grown in DMEM medium (GIBICO, USA) supplemented with 10% heat-activated fetal bovine serum (FBS, GIBICO, USA) and 1% penicillin/streptomycin (P/S, GIBCO, USA) in a humidified atmosphere of 95% air and 5% $CO_2$ at 37° C.

To determine the cellular tyrosinase activity, B16 cells are seeded in 24-well plates ($4 \times 10^4$ cells/well) and allowed to adhere overnight. After treated with different drugs or blank medium for 48 hours, the cells are washed with ice-cold phosphate buffer saline (PBS, pH 6.8) (GIBICO, USA) twice and then lysed in 150 μL of PBS (pH 6.8) containing 0.1% Triton X-100 by freeze-thaw at −20° C. for three times. After transferring into 1.7 mL Eppendorf tube, the cell lysates are centrifuged at 15,000×g for 10 min at 4° C. An aliquot of 50 μL supernatant is mixed with 50 μL $_L$-DOPA (Sigma-Aldrich, USA) solution (0.2% in PBS, pH 6.8) in a 96-well plate and incubated at 37° C. for 2 hours under darkness. Optical density of each sample is detected at 475 nm. All data are normalized with the protein content by each sample. The relative activity of cellular tyrosinase in B16 cells is calculated and presented as the percentage of the drug treated cells to that of the untreated cells (control group). All the data are normalized with the protein content by each sample.

To determine the cellular melanin production in B16 cells, B16 cells are seeded in 24-well plates and treated with different drugs with the same producer as describe in tyrosinase activity determination. After centrifugation, the melanin pellet is incubated with 100 μL of 1 N Sodium hydroxide solution (Sigma-Aldrich, USA) for 2 hours at 80° C. After cooling to room temperature, the solution is centrifuged at 15,000×g for 10 min. One-hundred micro-liter of the supernatant is transferred to a 96-well plate and detected at 405 nm. The amount of melanin in each sample is calculated by using the synthesized melanin as the reference and normalized with the protein content by each sample. Relative melanin content is calculated and presented as the percentage of the drug treated cells to that of the untreated cells (control group).

All experiments are performed in triplicate, and each experiment is repeated for at least 3 times in parallel. The results are presented as the mean±SD. Variance between two groups or more is evaluated by Student's t-test and one-way analysis of variance (one-way ANOVA), respectively. A p value of less than 0.05 is considered as a significant result for all tests.

The following examples illustrate the invention without limiting it in any way.

EXAMPLE 1

Extraction of *Atractylodis Macrocephalae Rhizoma, Glycyrrhizae Radix et Rhizoma, Angelicae sinensis Radix, Paeoniae Radix Alba* and *Poria*

The herbal formula composes of *Atractylodis Macrocephalae Rhizoma, Glycyrrhizae Radix et Rhizoma, Angelicae sinensis Radix, Paeoniae Radix Alba* and *Poria* with the weight ratio of 2:1:3:2:2.

Twenty five grams of the blend herbal formula is soaked with 250 mL distilled water for 1 h, extracted under reflux for 4 hours and then filtered to obtain a first herbal extract. The herbal residuals of the first extract are further reflux-extracted with 8-, followed by 5-fold volume (v/w) of distilled water for 2 hours and 1 hour to obtain the second and third herbal extracts, respectively. The second and third extracts are combined with the first herbal extract to form a combined extract. The combined extract is concentrated under reduced pressure to a suitable volume (~25 mL) to form a concentrated extract. After cooling, the concentrated extract is loaded onto a macroporous resin (D101) column (~50 mL) and allowed for statically-adsorbing for 4 hours. Subsequently, the concentrated extract is washed with distilled water (10-fold column volume) and then eluted with 8-fold column volume of 95% or 60% ethanol to form a first eluent and second eluent, respectively. Each eluent is concentrated under reduced pressure to remove the ethanol and then lyophilized with a Virtis Freeze Dryer (The VirTis Company, New York, USA) to obtained Sample 1 and Sample 2.

Twenty five grams of the blend herbal formula is soaked with 250 mL distilled water for 1 hour, extracted under reflux for 4 hours and then filtered to obtain the herbal extract. The herbal extract is concentrated under reduced pressure to form a concentrated extract. After cooling, the concentrated extract is loaded onto a macroporous resin (D101) column (~50 mL), allowed for statically-adsorbing for 4 hours, washed with distilled water (10-fold column volume) and then eluted with 8-fold column volume of 95% or 60% ethanol to form the third and forth eluents, respectively. Each eluent is concentrated under reduced pressure to remove the ethanol and then lyophilized with a Virtis Freeze Dryer (The VirTis Company, New York, USA) to obtained Sample 3 and Sample 4.

The weight of each sample 1-4 is weighted and recorded. The yield percentages for Sample 1 to 4 are calculated and expressed as the weight ratio of each fraction to that of the herbs. As shown in Table 1, Sample 1 is selected for further study since the yield (%) was the highest.

TABLE 1

Effect of extraction method on percentage of sample yield.

| Sample | Herb weight (g) | Fraction weight (g) | Yield percentage (%) |
| --- | --- | --- | --- |
| 1 | 25 | 0.65 | 2.6 |
| 2 | 25 | 0.61 | 2.4 |
| 3 | 25 | 0.55 | 2.2 |
| 4 | 25 | 0.50 | 2.0 |

EXAMPLE 2

Comparison on Tyrosinase Inhibition by Different Herbal Formulas

Four different herbal formulae composed of *Atractylodis Macrocephalae Rhizoma*, *Glycyrrhizae Radix et Rhizoma*, *Angelicae sinensis Radix*, *Paeoniae Radix Alba* and *Poria* are used in this example. The composition of each formula is shown in Table (2a). The only difference of preparing Sample 5 to 7 is that the weight of *Angelicae sinensis Radix* in Sample 5, 6 and 7 are 15 g, 40 g and 75 g respectively. The preparation of sample 5, 6 or 7 is the same as that for sample 1 as described in EXAMPLE 1. The inhibitory effects of each sample at 200 μg/mL (lower than the sub-lethal concentration) on cellular tyrosinase activity in B16 cells are determined and compared. As shown in Table (2b), Sample 1 gave the best inhibitory effect on cellular tyrosinase activity in B16 cells.

TABLE (2a)

Compositions of Samples 1, 5, 6 and 7.

| Herb | Sample 1 weight (g) | Sample 5 weight (g) | Sample 6 weight (g) | Sample 7 weight (g) |
| --- | --- | --- | --- | --- |
| Atractylodis Macrocephalae Rhizoma | 20 | 20 | 20 | 20 |
| Glycyrrhizae Radix et Rhizoma | 10 | 10 | 10 | 10 |
| Angelicae sinensis Radix | 30 | 15 | 40 | 75 |
| Paeoniae Radix | 20 | 20 | 20 | 20 |
| Poria | 20 | 20 | 20 | 20 |

TABLE (2b)

Effects of Samples 1, 5, 6 and 7 on cellular tyrosinase activity in B16 cells. Data are expressed as mean ± SD (n = 3)

| Sample | Relative tyrosinase activity (%) | Relative melanin production (%) |
| --- | --- | --- |
| 1 | 74.9 ± 12.5 * | 89.6 ± 6.9 * |
| 5 | 92.7 ± 4.0 | 100.8 ± 5.3 |
| 6 | 85.2 ± 0.4 * | 89.7 ± 17.5 * |
| 7 | 85.4 ± 11.3* | 94.8 ± 8.2 |

Remark:
* $p < 0.05$ vs control and
** $p < 0.01$ vs control.

EXAMPLE 3

Effects of Sample 1 on Cellular Tyrosinase Activity and Melanin Production in B16 Cells The dose-dependently inhibitory effects of Sample 1 (formulated and prepared as described in EXAMPLE 1) on cellular tyrosinase activity and melanin production are determined in B16 cells.

B16 cells are seeded in 24-well plates ($4 \times 10^4$ cells/well) and allowed to adhere overnight. The cells are treated with different concentrations of Sample 1 (150, 200 and 300 μg/mL, lower than the sub-lethal concentration determined by MTT assay) for 48 hours. Thereafter, the cellular tyrosinase activity and melanin content are determined as described above. In addition, kojic acid (35.5 and 71.0 μg/mL), a tyrosinase inhibitor used in various cosmetic products, is included as positive control.

Figure 2:
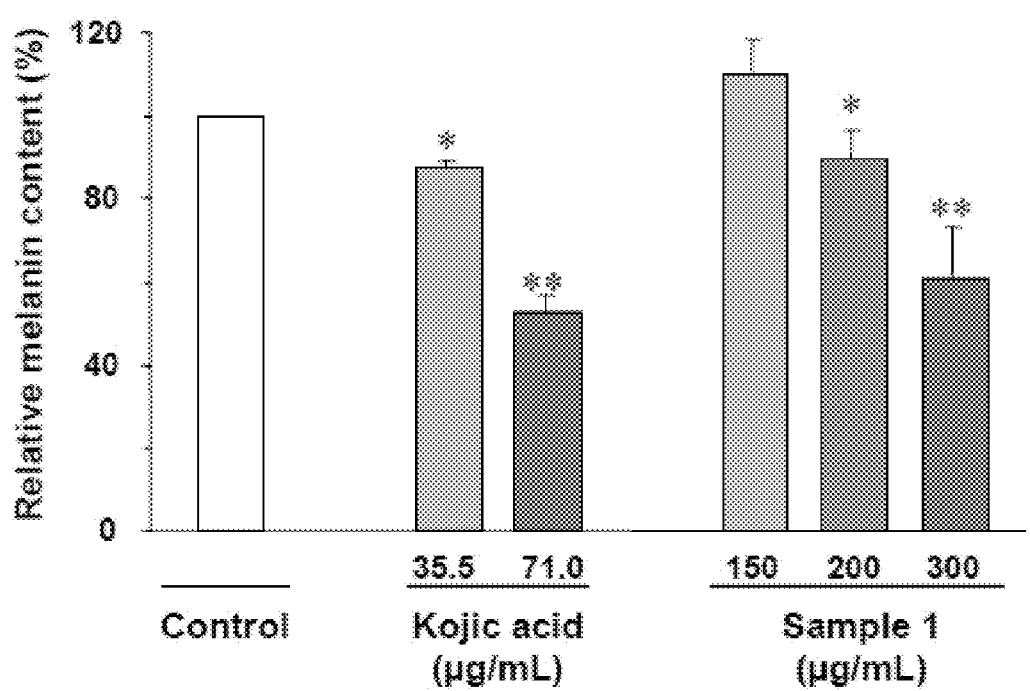
FIG. 2 shows the dose-dependently inhibitory effect of an embodiment of the herbal extract (sample 1 in Table 2a) on cellular melanin content in B16 cells. Kojic acid is used as positive control. Data are expressed as Mean±SD (n=3). *$p<0.05$ vs control; **$p<0.01$ vs control.

As illustrated in FIG. 1 and FIG. 2, Sample 1 dose-dependently inhibits cellular tyrosinase activity and melanin production in B16 cells. These effects of Sample 1 are comparative to that of kojic acid.

EXAMPLE 4

Free Radical Scavenging Activity of Sample 1

The free radical scavenging activity of Sample 1 is determined by DPPH free radical scavenging test. Briefly, 50 μL of Sample 1 solution (40, 70 and 100 μg/mL in 50% methanol) or Rutin solution (positive control; 10 and 20 μg/mL in 50% methanol) is mixed with 150 μL DPPH solution (0.15 mM in methanol) in a 96-well plate. The mixture is incubated for 30 min in dark under moderate shacking. Optical density of each sample is detected at 517 nm and DPPH scavenging activity is calculated by the following equation: Inhibition (%)=[(Absorbance of control−Absorbance of sample)/(Absorbance of control)]×100. Each treatment is performed in triplicate and repeated for 3 times in parallel. All data were expressed as mean±SD (n=3).

Figure 3:
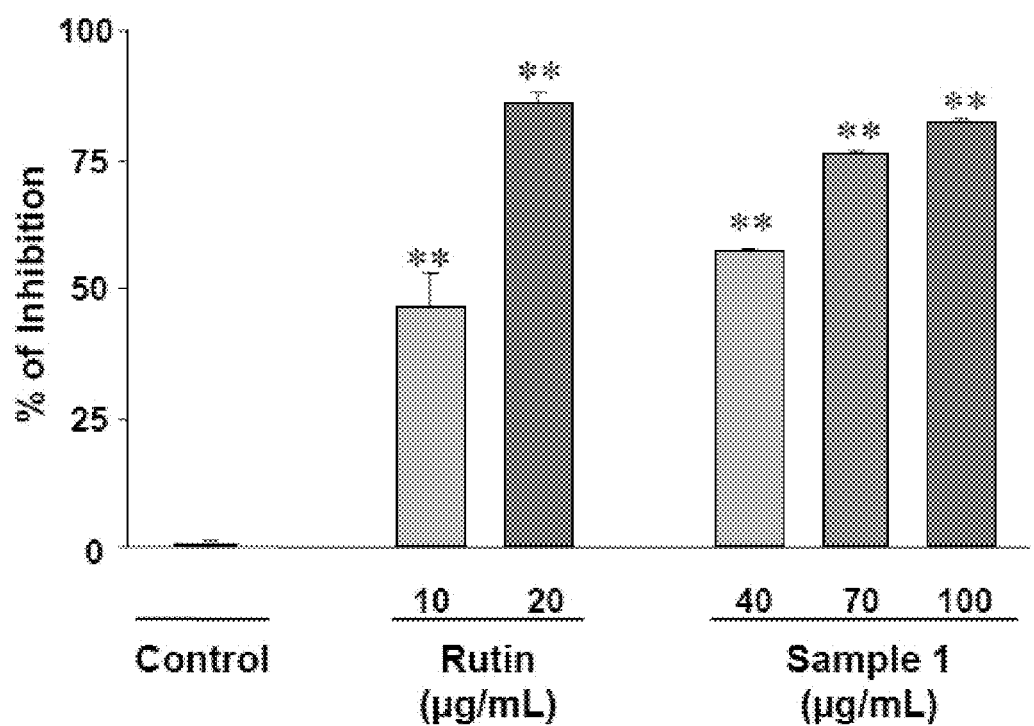
FIG. 3 shows the DPPH scavenging activity of an embodiment of the herbal extract (sample 1 in Table 2a). Rutin is used as positive control. Data are expressed as Mean±SD (n=3). *$p<0.05$ vs control; **$p<0.01$ vs control.

As illustrated in FIG. 3, dose-dependent anti-oxidative activity of sample 1 is demonstrated, hence the use of Sample 1 as an anti-skin-aging agent.

EXAMPLE 5

Sunscreen Function of Sample 1

UV radiation is one of the main factors which induce skin pigmentation and aging. UV irradiation can increase the release of α-melanocyte-stimulating hormone (α-MSH) from skin cells thus stimulating melanin synthesis in melanocytes and; increase the generation of free radicals in skin thus developing oxidative stress-induced skin aging. Therefore, sunscreen is an adjuvant function to help skin-whitening and anti-skin-aging.

Figure 4:
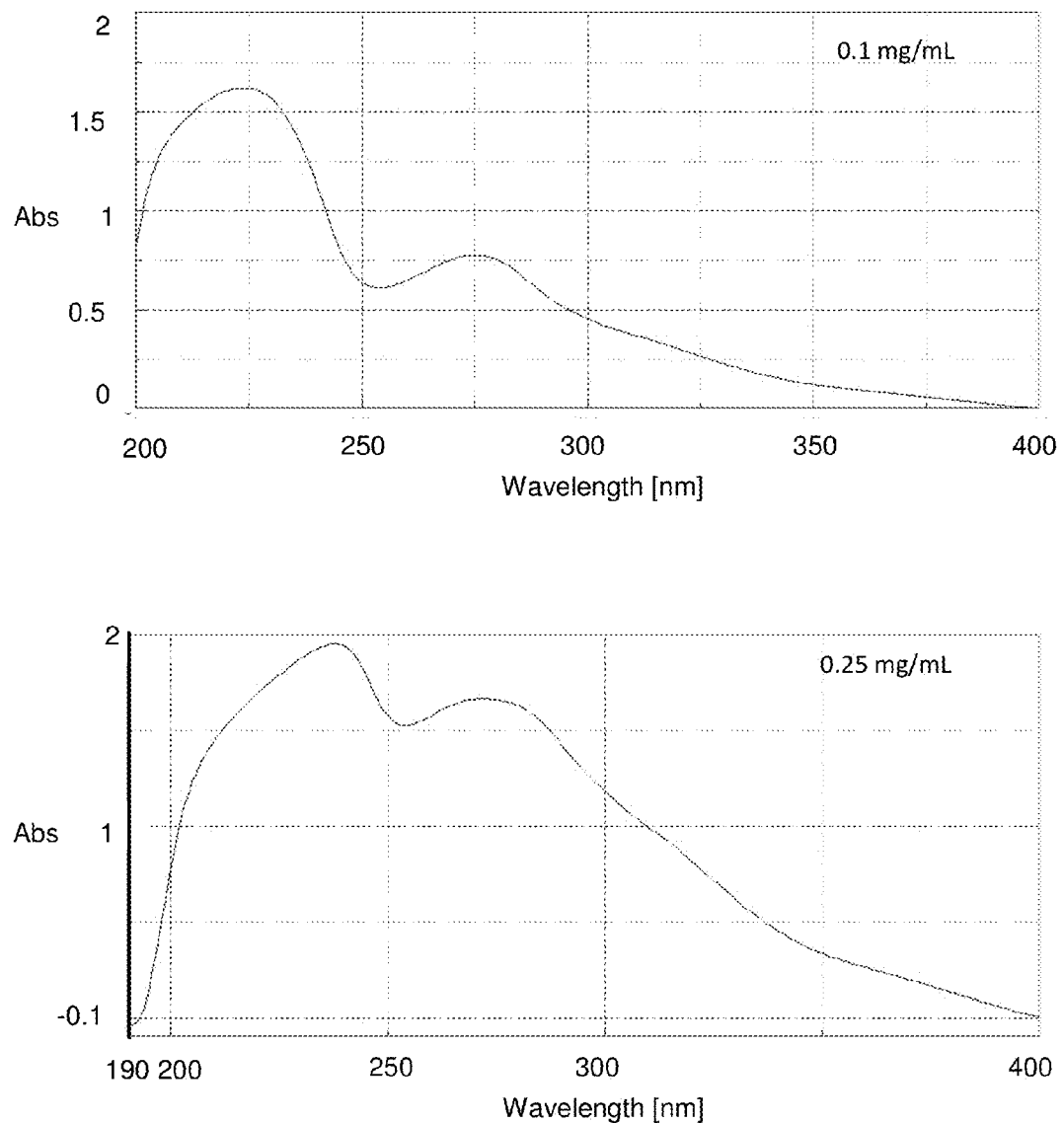
FIG. 4 shows the UV absorbance profiles (200-400 nm) of an embodiment of the herbal extract (sample 1 in Table 2a) at the concentrations of 0.1 mg/mL (top) and 0.25 mg/mL (bottom), respectively.

The sunscreen function of Sample 1 is measured by UV spectrophotometric method. Sample 1 is dissolved in 25% methanol at the concentration of 0.10 mg/mL and 0.25 mg/mL. The UV absorbance profile of each sample between the wavelengths from 200 to 400 nm is measured using a UV-visible spectrophotometer. As illustrated in FIG. 4, Sample 1 absorbs UV light at both concentrations. The data shows the UV absorption characteristic of Sample 1 for use as a sunscreen.

INDUSTRIAL APPLICABILITY

The present invention discloses a composition comprising *Atractylodis Macrocephalae Rhizoma, Glycyrrhizae Radix et Rhizoma, Angelicae sinensis Radix, Paeoniae Radix Alba* and *Poria* for skin care. More particularly, the composition relates to inhibitory effects on cellular tyrosinase activity and melanin production, scavenging of free radical and UV absorption.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extend. All publications recited herein are hereby incorporated by reference in their entirety.

What we claim:

1. A method for inhibiting tyrosinase activity and melanin production in an animal to improve skin appearance comprising applying a composition consisting essentially of an extract with a weight yield percentage of at least 2.6 obtained from an herbal formula consisting of *Atractylodis macrocephalae rhizoma, Glycyrrhizae radix et rhizoma, Angelicae sinensis radix, Paconiae radix alba* and *Poria* in a dry weight ratio of 2:1:3:2:2.

2. The method according to claim 1 wherein the animal is a human and said applying comprises topical administration.

3. The method of claim 1, wherein said composition is applied to the subject in need thereof in the form of a day cream, a night cream, a face lotion, a body lotion, a body butter, a skin peel, a mask, a shower gel, a sun cream, a sun lotion, an after sun cream or an after sun lotion.

4. The method of claim 1, wherein said improving skin appearance comprises anti-skin ageing or skin-whitening.

* * * * *